United States Patent [19]

Seidl et al.

[11] Patent Number: 5,000,024
[45] Date of Patent: Mar. 19, 1991

[54] ROLLING MILL DRIVE WITH SPINDLES RELEASABLY ARRANGED BETWEEN PINIONS AND WORK ROLLS

[75] Inventors: Karl-Heinz Seidl, Hilchenbach; Gerhard Pithan, Netphen; Jürgen Stelbrink, Hilchenbach, all of Fed. Rep. of Germany

[73] Assignee: SMS Schloemann-Siemag Aktiengesellschaft, Dusseldorf, Fed. Rep. of Germany

[21] Appl. No.: 300,963

[22] Filed: Jan. 23, 1989

[30] Foreign Application Priority Data

Jan. 22, 1988 [DE] Fed. Rep. of Germany ....... 3801749

[51] Int. Cl.[5] ............................................ B21B 35/14
[52] U.S. Cl. ...................................... 72/249; 72/444; 74/109; 74/422; 403/349; 464/109; 464/901
[58] Field of Search ................... 72/249, 444; 403/322, 403/325, 348, 349; 464/109, 901; 74/29, 109, 422

[56] References Cited

U.S. PATENT DOCUMENTS

| 3,040,717 | 6/1962 | Rumsey | 74/109 |
| 3,334,505 | 8/1967 | Boiko et al. | 72/239 |
| 4,464,141 | 8/1984 | Brown | 464/159 |
| 4,586,392 | 5/1986 | Nilsson | 74/109 |

FOREIGN PATENT DOCUMENTS 2187820 9/1987 United Kingdom ............... 403/349

Primary Examiner—Lowell A. Larson
Assistant Examiner—T. C. Schoeffler
Attorney, Agent, or Firm—Toren, McGeady & Associates

[57] ABSTRACT

A rolling mill drive with spindles arranged axially slidably between pinions and work rolls. A joint of each spindle is releasably connected to the neck of at least one roll, particularly the work roll. At least the spindle joint connected to the work roll includes a coupling and uncoupling device, preferably an annular bayonet-type coupling device.

10 Claims, 3 Drawing Sheets

5,000,024

ROLLING MILL DRIVE WITH SPINDLES RELEASABLY ARRANGED BETWEEN PINIONS AND WORK ROLLS

BACKGROUND OF THE INVENTION

1. Field of the Invention

The present invention relates to a rolling mill drive with joint spindles arranged axially slidably between pinions and work rolls. A joint of each spindle is releasably connected to the neck of at least one roll, particularly of the work roll.

2. Description of the Related Art

In conventional rolling mill stands, the work rolls between which the material to be rolled is worked, for example, a metal strip to be cold-rolled, are driven by drive spindles which are connected to the necks of the work rolls. The drive spindles are connected to driving pinions. The pinions are driven by suitable drive motors with transmissions being arranged between the pinions and the drive motors. At the connections to the work rolls and the pinions, the drive spindles have joints, usually universal joints, for compensating angular displacements caused by varying thicknesses of the strip being rolled.

Since in normal rolling operation, the work rolls must meet high requirements and must be frequently exchanged because of the occurring wear and because of necessary adjustments to the respective rolling program, special structural provisions are made for separating the work rolls and spindles from each other. In known separating devices, the exchange of the rolls including the removal of the necks, of the sliding pieces and the pulling-off of the spindle are very cumbersome and require substantial time and operations.

U.S. Pat. No. 3,670,587 discloses a vertical rolling mill in which the rolls are exchanged by pulling two rolls apart from each other and then moving the rolls downwardly and pulling the rolls with the necks thereof out of the couplings of the drive units. However, this requires expensive and complicated arrangements for displacing and axially moving the work rolls. If the couplings of the drive units are not fixed in their position after the necks have been pulled out, the subsequent insertion of the necks of the new rolls into the coupling is very difficult.

German Offenlegungsschrift 27 33 988 discloses a drive arrangement for vertical rolling mill rolls. The drive arrangement includes a drive shaft which is releasably connected through a universal joint to the neck of a roll. An inner shaft and an outer shaft connected with the inner shaft are mounted so as to be axially displaceable. For coupling the neck of the rolling mill roll with and for uncoupling the neck of the roll from the corresponding yoke of the universal joint of the drive shaft, a positioning unit is provided which acts on the inner shaft and the outer shaft and which includes a pressure medium cylinder fastened to the outer shaft and a piston rod mounted on the inner shaft. For actuating the pressure medium cylinder, the outer shaft is moved onto the inner shaft and, thus, the shaft is shortened until the coupling yoke of the universal joint is pulled off the roll neck. This known arrangement for pulling off rolls is of complicated construction. The drive shaft is constructed in two pieces. Also, a separate device is required for fixing the shaft after the uncoupling from the roll. A separate device consists of spring arrangements, support rods, etc. which make it difficult to quickly and precisely couple an uncouple the drive shaft and the rolling mill row.

It is, therefore, the primary object of the present invention to improve the rolling mill drive of the above-described type by means of a simple, compact and very accurately adjustable structural arrangement, so that the replacement of the work rolls and the separation of the work roll and the spindle is made simpler and can be carried out more quickly than in the past. Particularly high requirements are to be met with respect to the precision of the exchange in order to reduce the loads acting on the roll bearing and the spindle joint during the roll exchange as much a possible.

SUMMARY OF THE INVENTION

In accordance with the present invention, in the rolling mill drive of the type described above, at least the spindle joint connected to the work roll includes a coupling and uncoupling device, preferably an annular bayonet-type coupling device.

The arrangement of the coupling and uncoupling device within the spindle joint results in a very compact construction. The use of an annular bayonet-type coupling device is particularly advantageous because it makes possible a precise and quick coupling and uncoupling of work roll and spindle. The resulting precision and accuracy of the mechanically releasable connection of roll and spindle prevents uncontrolled loads on the roll bearing and on the transmission elements of the spindle joint, so that the service life and the availability of the structural elements are not impaired.

In accordance with an advantageous feature of the present invention, the annular bayonet-type coupling device serves to couple the neck of the work roll to the joint sleeve of the spindle joint, so that an internal toothing of the sleeve can interact with a curved toothing of a wobbler arranged on the spindle shaft.

In accordance with a further development of the invention, the closing journal of the annular bayonet-type coupling is arranged concentrically and in axial alignment with an end face of the neck of the work roll. The closing journal is engaged by a closing wheel which is connected to the joint sleeve and is mounted so as to be rotatable within the joint sleeve. As a result of this development, the coupling and uncoupling device is integrated in a particularly favorable manner in the spindle joint and it is apparent that an extremely compact and space-saving, releasable connection between spindle joint and neck of the work roll is provided.

In accordance with another advantageous further development of the invention, the closing journal has an external toothing which engages the internal toothing of the closing wheel.

In accordance with another advantageous feature of the invention, the external toothing of the closing journal is undercut in such a way that the undercut forms an annular groove in which the internal toothing of the closing wheel is rotatably guided, so that, for coupling the coupling device, the internal teeth of the closing wheel can be rotated so as to be in axial alignment and in positive engagement behind the external teeth of the closing journal and that, for uncoupling the coupling device, the internal teeth of the closing wheel can be rotated so as to be in axial alignment with the tooth gaps of the external toothing of the closing journal. This arrangement makes possible an exact axial fixing of the neck relative to the spindle joint and, thus, an exact alignment of the roll axis relative to the spindle axis. This is one of the requirements for safely transmitting the high torques from the spindle shaft through wobbler and joint sleeve to the roll after the rolls have been exchanged.

To be able to actuate the annular bayonet-type closing device arranged in the spindle joint in a simple manner, another further development of the invention provides that the closing wheel of the bayonet-type coupling device has an external toothing which engages an adjusting device for effecting the rotary movement of the closing wheel.

The adjusting device may include at least one plunger with external toothing which is guided in a guide bore within the joint sleeve approximately tangentially relative to the closing wheel and which is adjustable from outside the joint sleeve. The plunger has essentially a round shape and has on its outer surface a toothing in the form of a rack which engages the external toothing of the closing wheel, so that a displacement of the plunger by a certain distance results in an exactly corresponding rotation of the closing wheel. As a result of this measure the position of the toothing of the closing journal of the closing wheel always and accurately corresponds to the opening and closing positions of the bayonet-type closing device.

For an accurate adjustment and limiting of the adjustment path of the plunger, the plunger advantageously includes a hollow cylinder with an inner plunger shaft which is surrounded by plate springs. The plunger shaft, in turn, is slidingly held in the guide bore of the joint sleeve in a fixedly arranged stop for the hollow cylinder. The play of movement between the plunger, preferably between the hollow cylinder of the plunger and the stop, is adjustable in accordance with the required angle of rotation between the closing journal and closing wheel.

Finally, in accordance with another further development of the invention, the pretensioned spring unit predetermines the play of movement between the lower rim of the hollow cylinder and the stop. Also, an adjusting unit, preferably a hydraulic piston-cylinder unit, for adjusting the plunger against the force of the spring toward the stop, is mounted so as to act on the outwardly directed surface of the cylinder head. These measures according to the present invention have the advantageous result that, in the position of the plunger in which the plunger is pretensioned by the spring unit, the closing wheel of the bayonet-type closing device is turned in such a way that the internal teeth of the closing wheel are located in axial alignment and with positive engagement behind the external teeth of the closing journal. On the hand, when the plunger is forced by the adjusting unit up to the stop into the guide bore against the force of the plate springs, the teeth of the plunger turn the closing wheel by a defined angle until the internal teeth of the closing wheel are in axial alignment with the tooth gaps of the external toothing of the closing journal, so that a problem-free uncoupling of the closing wheel and closing journal is ensured.

The various features of novelty which characterize the invention are pointed out with particularity in the claims annexed to and forming a part of this disclosure. For a better understanding of the invention, its operating advantages and specific objects attained by its use, reference should be had to the drawings and descriptive matter in which there is illustrated and described a preferred embodiment of the invention.

DESCRIPTION OF THE PREFERRED EMBoDIMENT

Figure 1:
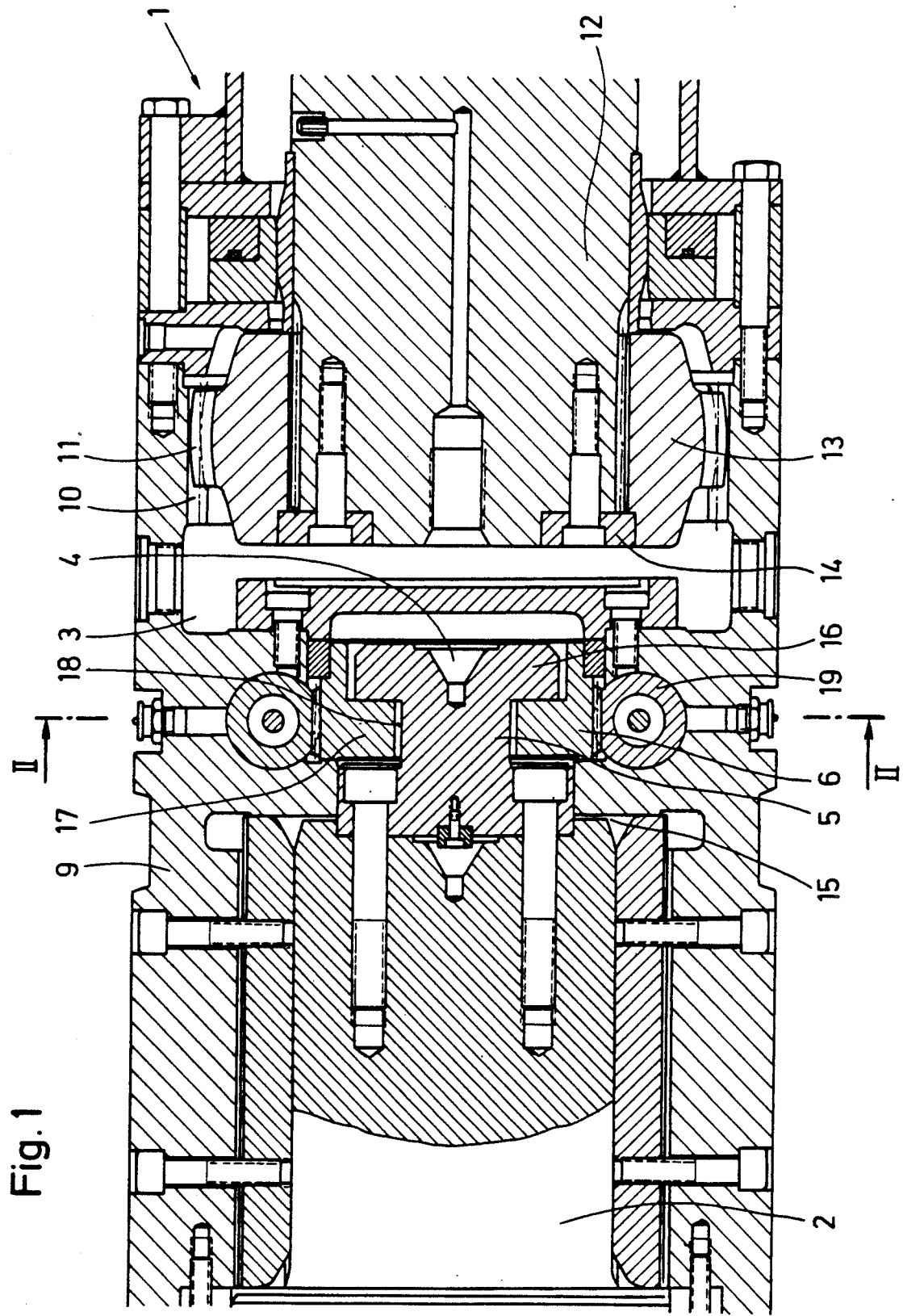
FIG. 1 is a sectional view of an annular bayonet-type closing device arranged in a spindle joint.

The rolling mill drive illustrated in FIG. 1 of the drawing includes joint spindles 1 which are arranged between pinions and work rolls. The spindles 1 are axially slidable and releasably connected to the necks 2 of the work rolls. The spindle shown in FIG. 1 has a spindle joint 3 in which is arranged an annular bayonet-type closing device 4 for coupling and uncoupling the work roll and the spindle.

The bayonet-type closing device 4 includes a closing journal 5, a closing wheel 6 and an adjusting device 7 which is actuated outside of the spindle joint 3 by means of an adjusting unit 8. The bayonet-type closing device 4 couples the neck of the work roll with the joint sleeve 9 of the joint 3. An internal toothing 10 of the joint sleeve interacts with a curved toothing 11 of a wobbler 13 arranged on the spindle shaft 12. The wobbler 13 is arranged on the spindle shaft 12 so as to rotate therewith, for example, by means of a key and groove connection 14.

The closing journal 5 of the bayonet-type closing device 4 is fastened concentrically and in axial alignment by means of a screw connection to the end face 15 of the neck 2 of the work roll. The closing wheel 6 of the bayonet-type closing device 4 engages in the closing journal 5. The closing wheel 6 is rotatably held in the sleeve 9 of the spindle joint 3. The closing journal 5 has an external toothing 16 and the closing wheel 6 has an internal toothing 17. The external toothing 16 of the closing journal 5 is undercut in such a way that an annular groove 18 is formed by the undercut. The closing wheel 6 is guided in the annular groove 18.

Figure 2:
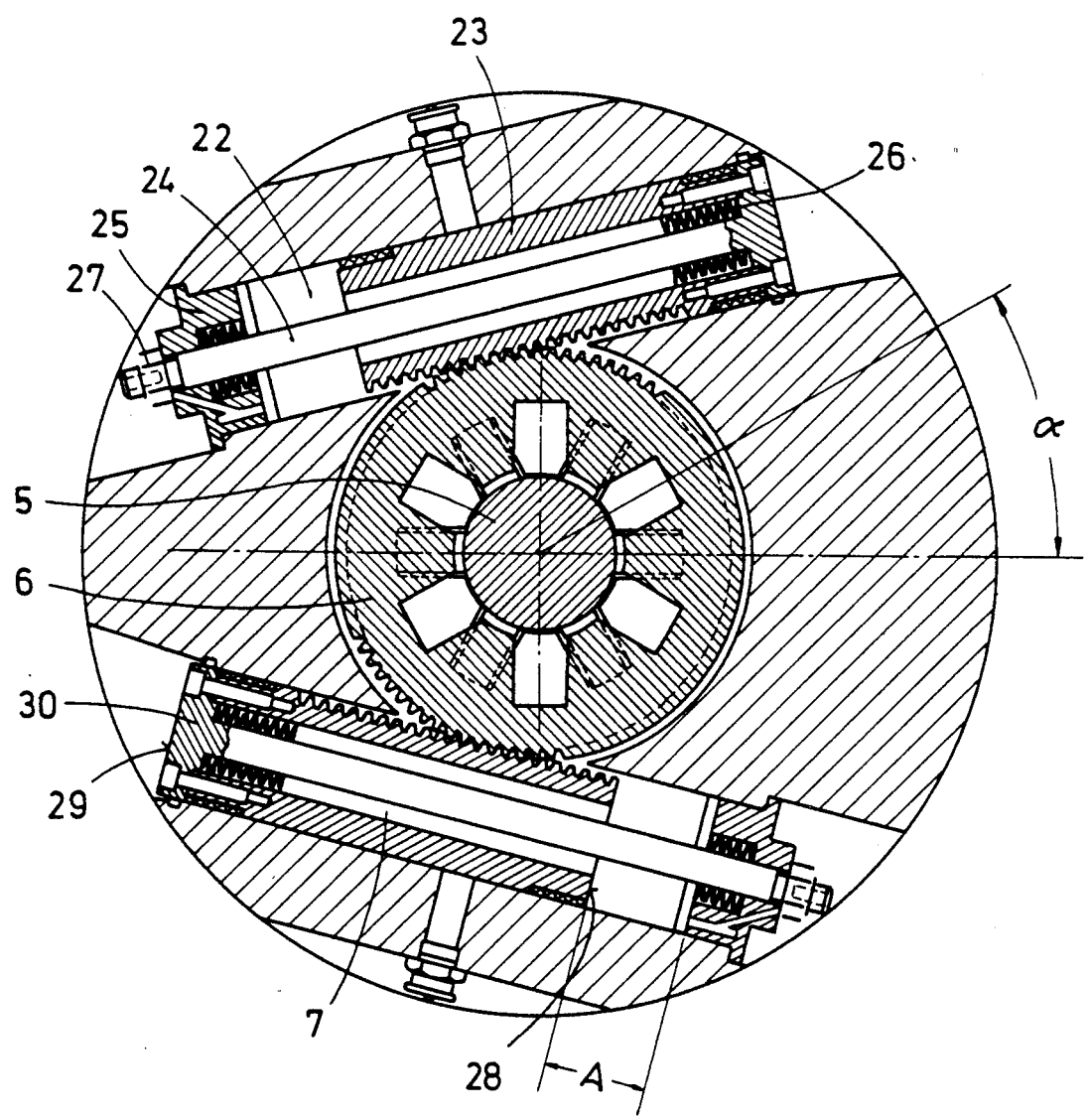
FIG. 2 is a sectional view taken along sectional line II—II of FIG. 1 of the closed bayonet-type closing device and an adjusting device.

The closing wheel 6 is rotatable in the annular groove 18, so that, when the bayonet-type closing device is closed, the internal teeth 17 of the closing wheel are turned in axial alignment and with positive engagement behind the external teeth 16 of the closing journal 5, as shown in FIG. 2. In this closed position of the bayonet-type closing device, the spindle 1 is axially fixedly connected to the neck 2 of the work roll. Furthermore, by means of a suitable connection which is not shown in detail, the joint sleeve 9 is radially tightly connected to the neck 2, so that the drive torque is transmitted to the neck 2 and, thus, to the work roll from the spindle shaft 12 through the wobbler 13 with the curved toothing 11 and the joint sleeve 9 with the internal toothing 10.

Figure 3:
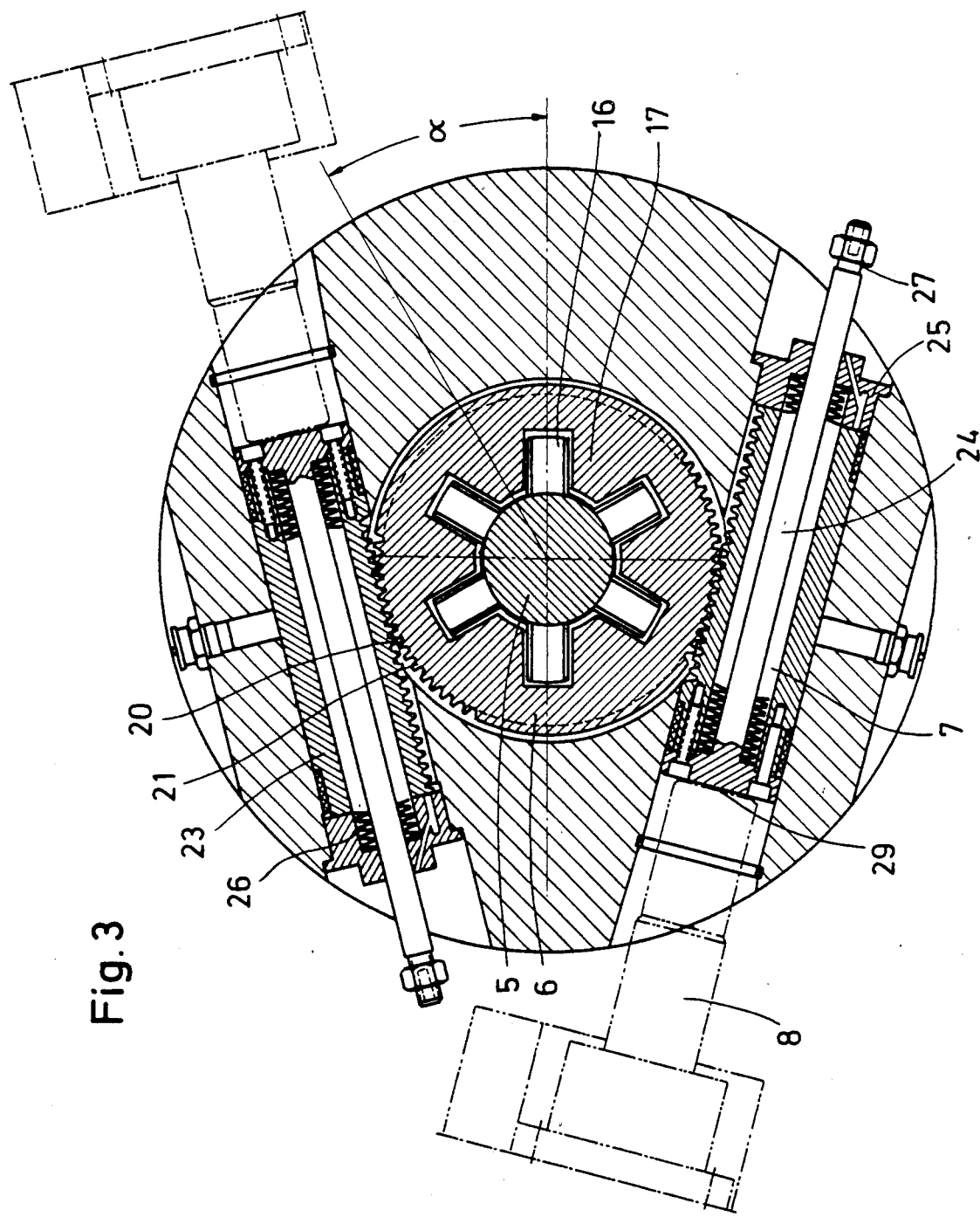
FIG. 3 is a sectional view taken along sectional line II—II of FIG. 1 of the open bayonet-type closing device and the adjusting device.

For an exact and quick coupling and uncoupling of the bayonet-type closing device arranged in the spindle joint, a special adjusting device 7 shown in FIGS. 2 and 3 is used. The adjusting device 7 makes it possible to actuate the bayonet-type closing device from outside of the joint sleeve. For this purpose, the adjusting device 7 has two externally toothed plungers 19 the teeth 20 of which are in engagement with the external toothing 21 of the closing wheel 6. Each plunger 19 is guided in a guide bore 22 within the joint sleeve 9 approximately tangentially relative to the closing wheel and each plunger 19 is slidable from the outside of the joint sleeve.

The plunger is formed by a hollow cylinder 23 and a plunger shaft 24 which, in turn, is slidably mounted in the guide bore 22 in a fixedly arranged stop 25. A spring unit formed by plate springs 26 is arranged in the hollow cylinder 23 and around the plunger shaft 24. The play of movement A between the plunger 19, i.e., the lower rim 28 of the hollow cylinder 23, and the stop 25 is adjustable in accordance with the required angle of rotation α between the closing journal 5 and the closing wheel 6 of the bayonet-type closing device 4. The adjustment is effected by means of a knurled-head screw 27 provided at the end of the plunger shaft.

The hollow cylinder 23 is held spaced apart from the stop 25 by means of the plate spring 26, so that the pretensioned spring unit determines the play of movement A between the lower rim of the hollow cylinder and the stop. The outwardly directed surface 29 of the cylinder head 30 can be connected to adjusting unit 8. The adjusting unit 8 advantageously is a hydraulic piston-cylinder unit. The adjusting unit displaces the plunger 19 against the force of the plate springs 26 up to the stop 25.

As illustrated in FIG. 3 of the drawing, the plunger 19 is displaced by means of the adjusting unit 8 against the stop 25. In the position shown in FIG. 3, the plunger has turned the closing wheel 6 of the bayonet-type closing device to such an extent that the internal teeth of the closing wheel 6 are in axial alignment with the tooth gaps of the external teeth of the closing journal 5. Thus, in this position, the bayonet-type closing device 4 is open, i.e., the closing wheel 6 can be pulled in axial direction from the closing journal 5. The plunger 19 remains against the stop 25 during the uncoupling procedure.

For again axially locking the neck 2 and the sleeve 9 of the spindle joint 3, the plunger 19 is moved by the hydraulic adjusting unit 8 against the stop 25. As a result, the internal teeth of the closing wheel 6 are in alignment with the gaps of the external teeth of the closing journal 5, so that it is possible to slide the closing wheel in axial direction over the closing journal into the region of the annular groove 18. As soon as the closing wheel is guided in the annular groove 18, the hydraulic adjusting unit 8 is moved back and the plunger 19 is forced back by the fixedly adjusted, play of movement A into its initial position by means of the force of the plate springs 26. As a result, the closing wheel 6 is turned by the predetermined angle, so that the internal toothing of the closing wheel is rotated into axial alignment and with positive engagement behind the external teeth of the closing journal.

The measures according to the present invention described above make it possible to quickly and exactly connect and disconnect the work roll and the driving spindle 1 when the work rolls have to be replaced for reasons of wear or when the work rolls have to be adjusted to the production program being carried out.

While a specific embodiment of the invention has been shown and described in detail to illustrate the application of the inventive principles, it will be understood that the invention may be embodied otherwise without departing from such principles.

We claim:

1. A rolling mill drive including spindles, each spindle being arranged axially slidably between a pinion and a work roll, a joint of each spindle being releasably connected to the neck of at least one work roll, wherein the joint connected to the work roll includes a coupling and uncoupling device, and wherein the coupling and uncoupling device is an annular bayonet-type coupling device, the neck of the work roll having an end face, the bayonet-type coupling device including a closing journal and a closing wheel, the closing journal being arranged concentrically and in axial alignment with the end face of the neck of the work roll, the closing journal being engaged by the closing wheel, the spindle joint including a joint sleeve, the closing wheel being connected to the joint sleeve and being mounted so as to be rotatable within the joint sleeve, the closing journal having an external toothing and the closing wheel having an internal toothing, the external toothing of the closing journal engaging the internal toothing of the closing wheel, the closing wheel having an external toothing, an adjusting device being in engagement with the external toothing of the closing wheel for effecting the rotary movement of the closing wheel.

2. The rolling mill drive according to claim 1, wherein the spindle has a spindle shaft, a wobbler being arranged on the spindle shaft, the spindle joint including a joint sleeve, the annular bayonet-type coupling device coupling the neck of the work roll to the joint sleeve of the spindle joint, such that an internal toothing of the sleeve engages a curved toothing of the wobbler.

3. The rolling mill drive according to claim 1, wherein the external toothing of the closing journal is undercut, the undercut forming an annular groove, the internal toothing of the closing wheel being rotatably guided in the annular groove, the internal toothing of the closing wheel being rotatable between a first position in which the internal toothing of the closing wheel is in axial alignment with and in positive engagement behind the external toothing of the closing journal for coupling the coupling device, and a second position in which the internal toothing of the closing wheel is in axial alignment with gaps of the external toothing of the closing journal for uncoupling the coupling device.

4. The rolling mill drive according to claim 3, wherein the adjusting device includes at least one plunger with external toothing, the plunger being guided in a guide bore within the joint sleeve approximately tangentially relative to the closing wheel, the adjusting device being adjustable from outside the joint sleeve.

5. The rolling mill drive according to claim 4, wherein the plunger includes a hollow cylinder and a plunger shaft arranged in the hollow cylinder, a spring unit surrounding the plunger shaft, the plunger shaft being slidably mounted in the guide bore of the joint sleeves in a fixedly arranged stop for the hollow cylinder.

6. The rolling mill drive according to claim 5, wherein the spring unit includes a plurality of plate springs.

7. The rolling mill drive according to claim 5, wherein a play of movement exists between the hollow cylinder of the plunger and the stop, the play of movement being adjustable in accordance with a required angle of rotation between the closing journal and the closing wheel.

8. The rolling mill drive according to claim 7, the hollow cylinder having lower rim, the spring unit when in the pretensioned state predetermining the play of movement between the hollow cylinder and the stop, the hollow cylinder including a cylinder head with an outwardly directed surface, an adjusting unit for adjusting the plunger against the force of the spring unit toward the stop being mounted so as to act on the outwardly directed surface of the cylinder head.

9. The rolling mill drive according to claim 8, wherein the adjusting unit is the hydraulic piston-cylinder unit.

10. A rolling mill drive including spindles, each spindle being arranged axially slidably between a pinion and a work roll, a joint of each spindle being releasably connected to the neck of at least one work roll, wherein the joint connected to the work roll includes a coupling and uncoupling device, and wherein the coupling and uncoupling device is an annular bayonet-type coupling device, the spindle having a spindle shaft, a wobbler being arranged on the spindle shaft, the spindle joint including a joint sleeve, the annular bayonet-type coupling device coupling the neck of the work roll to the joint sleeve of the spindle joint, such that an internal toothing of the sleeve engages a curved toothing of the wobbler, the neck of the work roll having an end face, the bayonet-type coupling device including a closing journal and a closing wheel, the closing journal being arranged concentrically and in axial alignment with the end face of the neck of the work roll, the closing journal being engaged by the closing wheel, the closing wheel being connected to the joint sleeve and being mounted so as to be rotatable within the joint sleeve, the closing journal having an external toothing and the closing wheel having an internal toothing, the external toothing of the closing wheel journal engaging the internal toothing of the closing, the external toothing of the closing journal being undercut, the undercut forming an annular groove, the internal toothing of the closing wheel being rotatably guided in the annular grove, the internal toothing of the closing wheel being rotatable between a first position in which the internal toothing of the closing wheel is in axial alignment with and in positive engagement being the external toothing of the closing journal for coupling the coupling device, and a second position in which the internal toothing of the closing wheel is in axial alignment with gaps of the external toothing of the closing journal for uncoupling the coupling device, the closing wheel having an external toothing, an adjusting device being in engagement with the external toothing of the closing wheel for effecting the rotary movement of the closing wheel, wherein the adjusting device has an adjusting distance, the adjusting distance being adjustable in accordance with a required angle of rotation between the closing journal and the closing wheel.

* * * * *